US006949352B2

(12) United States Patent
Tardieux et al.

(10) Patent No.: US 6,949,352 B2
(45) Date of Patent: Sep. 27, 2005

(54) SERINE-THREONINE PHOSPHATASE PROTEIN OF A PARASITIC ORGANISM OF THE APICOMPLEXA PHYLUM, APPLICATIONS IN THERAPEUTICS

(75) Inventors: Isabelle Tardieux, Paris (FR); Violaine Delorme, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 267 days.

(21) Appl. No.: 10/147,874

(22) Filed: May 20, 2002

(65) Prior Publication Data

US 2003/0027237 A1 Feb. 6, 2003

Related U.S. Application Data

(60) Provisional application No. 60/291,609, filed on May 18, 2001.

(51) Int. Cl.[7] .............................. C12Q 1/48; C12N 9/12
(52) U.S. Cl. ......................... 435/15; 435/194; 424/94.6
(58) Field of Search ........................... 424/94.6; 435/15, 435/194

(56) References Cited

PUBLICATIONS

Wester's II New Riverside Dictionary (1994) (houoghton Mifflin: Boston MA) p. 762 and 927.*
C.B. Mamoun, et al., Molecular Microbiology, vol. 39, No. 4, pp. 973–981, XP–002229525, "Plasmodium Protein Phosphatase 2C Dephosphorylates Translation Elongation Factor 1β and Inhibits its PKC–Mediated Nucleotide Exchange Activity in Vitro", Feb. 2001.

C.B. Mamoun, et al., The Journal of Biological Chemistry, vol. 273, No. 18, pp. 11241–11247, XP–002229526, "Identification and Characterization of an Unusual Double Serine/Threonine Protein Phosphatase 2C in the Malaria Parasite Plasmodium Falciparum", May 1, 1998.

O. Poupel, et al., Molecular Biology of the Cell, vol. 11, pp. 355–368, XP–002229527, "Toxoflin, A Novel Actin–Binding Protein from Toxoplasma Gondii, Sequesters Actin Monomers and Caps Actin Filaments", Jan. 2000.

V. D. Delorme, Database EMBL Online!, Thesis 2002 Dpt. Biol. Sci. Univ. VII, an Q8WPN9, p. 1, XP–002229528, "Serine–Threonine Phosphatase 2C. Toxoplasma Gondii", Mar. 1, 2002.

V. Delorme, et al., Molecular Biology of the Cell, vol. 14, pp. 1900–1912, "Actin Dynamics is Controlled by a Casein Kinase II and Phosphatase 2C Interplay on Toxoplasma Gondii Toxofilin", May 2003.

* cited by examiner

Primary Examiner—Jean C. Witz
Assistant Examiner—Susan Hanley
(74) Attorney, Agent, or Firm—Oblon, Spivak, McClelland, Maier & Neustadt, P.C.

(57) ABSTRACT

The present invention relates to a serine-threonine phosphatase protein of a parasitic organism of the Apixomplexa phylum and uses thereof.

8 Claims, 13 Drawing Sheets

```
1/1
ATG AAG TCC TCT GCT GAA ATT AGG CGG ACC ATG GAT GTC CCT CCT ACC ATT CAT GTA CCT CCA ACG TCG TAT CCC GCT TTC GAT
 M   K   S   S   A   E   I   R   R   T   M   D   V   P   P   T   I   H   V   P   P   L   P   P   T   S   Y   P   A   F   D
91/31                                  121/41                                        151/51
GCT GCC ATC TTC ACA GAC ATC GGT GGG CGC AAG CAT CAG GAA GAT AGG TTC ACT CTC TGT CCG CAG CTC GTT CCC GGC CGA GAC GAC TGC
 A   A   I   F   T   D   I   G   G   R   K   H   Q   E   D   R   F   T   L   C   P   Q   L   V   P   G   R   D   D   C
181/61                                        211/71                                  241/81
GCC TTC TTC GGT GTC TTC GAT GGC ACT GTT GGA GAT TTC GCC AGC GAA AAT GTC AAG GAT CTT GTT GTT CCA CAG TTG ATT TCC TCG CCC
 A   F   F   G   V   F   D   G   T   V   G   D   F   A   S   E   N   V   K   D   L   V   V   P   Q   L   I   S   S   P
271/91                                                     301/101                                  331/111
GCC TGG CAG GAG GTG ACT GAG ATG CTG AGA TCA GAC GTG CCC GCC ACC GAG GTG GAC GAG AAG CTC CCT CAG TTG CTT GAT CAG GCA GTC
 A   W   Q   E   V   T   E   M   L   R   S   D   V   P   A   T   E   V   D   E   K   L   P   Q   L   L   D   Q   A   V
361/121                                        391/131                                        421/141
GAT GAC ATG TAC AAG AAC GCA GAC AAC GAA CTT GTG AAG ATG TGC GAG CAG CTT AAC AAA GAC TAC GCC AGC AGT TCC GTC ACG GCC
 D   D   M   Y   K   N   A   D   N   E   L   V   K   M   C   E   Q   L   N   K   D   Y   A   S   S   T   S   V   T   A
451/151                                        481/161                                        511/171
GTC TTG GCC AAA GGC TTC GTG GCT GTT GGT CAT CTG GGC GAC AGC CGG ATC GCG ATG GGA GTC GAG ACG CCG AAC GGG TTG AAC TGC GAG
 V   L   A   K   G   F   V   A   V   G   H   L   G   D   S   R   I   A   M   G   V   E   T   P   N   G   L   N   C   E
541/181                                              601/201                                        631/211
TTC TTG ACC GTT GAC CAC AAG CCG GAT ATG CCA CAT GAG AAA CTG AGG AAA CTG CGC ATC ATG AGG AAT GGA GGC AGT GTT GAG TAT CTC CAC AAC CAC
 F   L   T   V   D   H   K   P   D   M   P   H   E   K   L   R   I   M   R   N   G   G   S   V   E   Y   L   H   N   H
661/221                                        691/231
AAC AAC CCG TTC ATT CGA GGC GGT GAC TTC TTC CGG AAG TCG CGG GAG CAG CCG ATG CAG CTC CAG TAC TCC CGA GCT TTG
 N   N   K   P   F   I   R   G   G   D   F   F   R   K   S   R   G   E   Q   P   M   Q   L   Q   Y   S   R   A   L
721/241                                              751/251                                              781/261
CGG GGG AAG GAC CTG AAG ATG TAC GGT CTG AGC AAT CAA CCC GAC GTA GAG ATC GCT ATG CAG GCC CGG AGA CAG GAA AGG AAC CCA GCG
 G   G   K   D   L   K   M   Y   G   L   S   N   Q   P   D   V   R   V   R   V   T   P   Q   H   R   V   M   I   L
811/271                                        841/281                                        871/291
GCG ACT GAT GGC TTG TGG GAC GTC ATG TTT GCG GCG CAA GCT GTA GAG ATC GCT ATG CAG GCG CAG GAA GGA AGG AAC CCA GCG CAT
 A   T   D   G   L   W   D   V   M   F   A   A   Q   A   V   E   I   A   M   Q   A   R   Q   E   G   R   N   P   A   Q
901/301                                              931/311                                  961/321
GCG CTG GTG GAG ATG ACC CTC GCT GAG CAG CAG CAG AGC CGC AAC CAA AGT GCA GAC AAC ATT ACT GCG ATG ACA GTG TTC TTC AAG ACT
 A   L   V   E   M   T   L   A   E   Q   Q   Q   S   R   N   Q   S   A   D   N   I   T   A   M   T   V   F   F   K   T
991/331
GAT TAG
 D   *
```

*FIG. 1*

Figure 2:
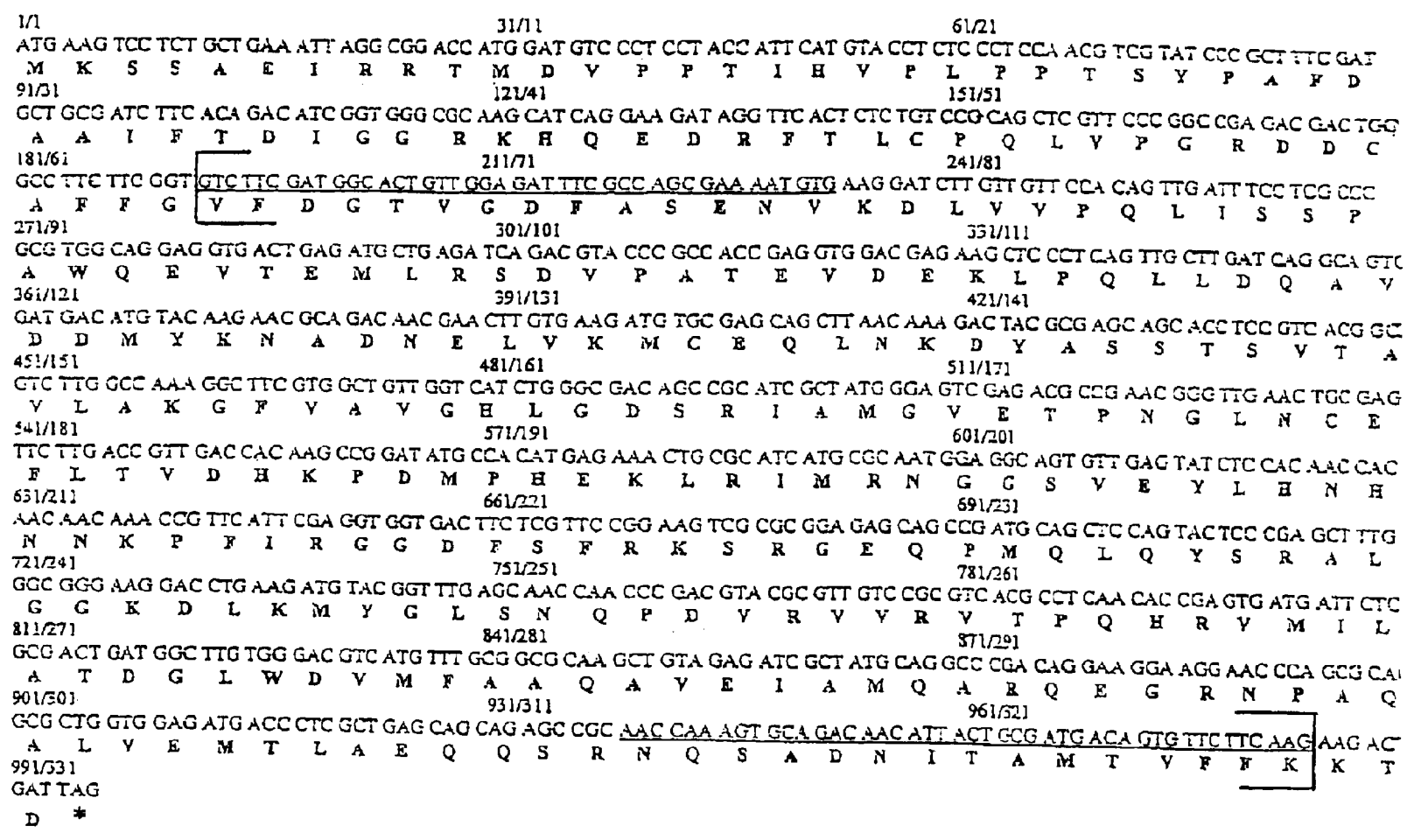

```
1/1
ATG AAG TCC TCT GCT GAA ATT AGG CGG ACC ATG GAT GTC CCT CCT ACC ATT CAT GTA CCT CTC CCT CCA ACG TCG TAT CCC GCT TTC GAT
 M   K   S   S   A   E   I   R   R   T   M   D   V   P   P   T   I   H   V   P   L   P   P   T   S   Y   P   A   F   D
91/31                                                                                       121/41                                                            151/51
GCT GCG ATC TTC ACA GAC TTC GGT GTC TTC GAT GGC ACT GTC TTC GAT GGC ACT GTC TTC GAT GGC AAG GAT CTT GTT CCA CAG TTG ATT TCC TCG CCC
 A   A   I   F   T   D   F   G   V   F   D   G   T   V   G   D   F   A   S   E   N   V   K   D   L   V   P   Q   L   I   S   S   P
271/91
...
```

```
Query=
        (331 letters)

Database: Homo sapiens protein sequences
          689,446 sequences; 217,131,788 total letters If you have any problems or questions with the results of this search
please refer to the BLAST FAQs Taxonomy reports Distribution of 9 Blast Hits on the Query Sequence
```

[Image]

```
                                                                    Score        E
Sequences producing significant alignments:                         (bits)
Value ref|NP_110395.1|  integrin-linked kinase-associated serine/t...      76    3e-14
ref|NP_003611.1|  protein phosphatase 1D magnesium-dependent...      70    2e-12
ref|NP_002697.1|  protein phosphatase 1B (formerly 2C), magn...      64    1e-10
ref|NP_066283.1|  protein phosphatase 1A (formerly 2C), magn...      60    2e-09
ref|NP_002698.1|  protein phosphatase 1G (formerly 2C), magn...      56    3e-08
ref|NP_055449.1|  KIAA0015 gene product [Homo sapiens] >gi|1...      50    3e-06
ref|NP_060914.1|  pyruvate dehydrogenase phosphatase [Homo s...      48    1e-05
ref|XP_008268.3|  KIAA1072 protein [Homo sapiens]                    46    3e-05
ref|NP_055721.1|  KIAA1072 protein [Homo sapiens]                    46    3e-05

Alignments

>ref|NP_110395.1| integrin-linked kinase-associated serine/threonine
>phosphatase 2C
          [Homo sapiens]
          Length = 392

Score = 76.3
 bits (186), Expect = 3e-14
  Identities = 72/278 (25%), Positives = 118/278 (41%), Gaps = 48/278 (17%)

Query: 61   AFFGVFDGTVGDFASENVKDLVVPQLISSPAWQEVTEMLRSDVPATEVDEKLPQLLDQAV 120
            ++F VFDG G  AS+    +  LI      +  + DV + E K      + +
Sbjct: 146  SYFAVFDGHGGIRASKFAAQNLHQNLIR--------KFPKGDVISVEKTVK------RCL 191

Query: 121  DDMYKNADNELVKMCEQLNKDYASSTSVTAVLA-KGFVAVGHLGDSRIAMGVETPNGLNC 179
            D +K+ D E +K         +    ++ T VLA    + + +LGDSR +
Sbjct: 192  LDTFKHTDEEFLKQASSQKFAWKDGSTATCVLAVDNILYIANLGDSRAILCRYNEESQKH 251

Query: 180  EFLTV--DHKPDMPHEKLRIMRNGGSVEYLHNHNNKPFIRGGDFSFRKSRGEQPMQLQYS 237
            L++  +H P     E++RI + GG+V                  G       L+ S
Sbjct: 252  AALSLSKEHNPTQYEERMRIQKAGGNVR------------------DGRVLGVLEVS 290
```

FIG. 3B

```
Query: 238 RALGGKDLKMYGLSNQFDVRVVRVTPQHRVMILATDGLWDVMFAAQAVEIAMQA------ 291
           R++G  K G+++ PD+R  ++TP R ++LA DGL+ V   +AV   +
Sbjct: 291 RSIGDGQYKRCGVTSVPDIRRCQLTPNDRFILLACDGLFKVFTPEEAVNFILSCLEDEKI 350

Query: 292 -RQEGRNPAQALVEMT---LAEQQSRNQSADNITAMTV 325
           +EG++ A A E    LA +  + SADN+T M V
Sbjct: 351 QTREGKSAADARYEAACNRLANKAVQRGSADNVTVMVV 388

>ref|NP_003611.1| protein phosphatase 1D magnesium-dependent, delta isoform
>[Homo
           sapiens]
           Length = 605

Score = 70.1
bits (170), Expect = 2e-12
 Identities = 59/205 (28%), Positives = 100/205 (48%), Gaps = 25/205 (12%)

Query: 144 SSTSVTAVLAKGF-VAVGHLGDSRIAMGVETP---NGLNCEFLTVDHKPDMPHEKLRIMR 199
           S T+ + V+ +G + V H+GDS + +G++       + +T DHKP++P E+ RI
Sbjct: 171 SGTTASVVIIRGMKMYVAHVGDSGVVLGIQDDPKDDFVRAVEVTQDHKPELPKERERIEG 230

Query: 200 NGGSVEYLHNHN-----NKPFIRGGDFSFRKSRGEQPMQLQYSRALGGKDLKMYG------ 249
           GGSV   N    +P +    R + +Q  L +RALG DL Y
Sbjct: 231 LGCSVMNKSCVNRVVWKRPRLTHNGPVRRSTVIDQIPFLAVARALG--DLWSYDFFSGEF 288

Query: 250 -LSNQPDVRVVRVTPQ-HRVMILATDGLWDVMFAAQAVEIAMQARQE-------GRNPAQ 300
           +S +PD V + PQ H+ +IL +DGLW+++  A+ +   ++     G++ A+
Sbjct: 289 VVSPEPDTSVHTLDPQKHKYIILGSDGLWNMIPPQDAISMCQDQEEKKYLMGEHGQSCAK 348

Query: 301 ALVEMTLAEQQSRNQSADNITAMTV 325
           LV   L  + R   ADN +A+  +
Sbjct: 349 MLVNRALGRWRQRMLRADNTSAIVI 373

>ref|NP_002697.1| protein phosphatase 1B (formerly 2C),
>magnesium-dependent, beta
           isoform; protein phosphatase 2C-beta [Homo sapiens]
 ref|XP_010821.2| protein phosphatase 1B (formerly 2C),
magnesium-dependent, beta
           isoform [Homo sapiens]
           Length = 479

Score = 64.3
bits (155), Expect = 1e-10
 Identities = 70/302 (23%), Positives = 122/302 (40%), Gaps = 49/302 (16%)

Query: 38  GGRKHQEDRFTLCPQLVPGRDDCAFFGVFDGTVGDFASENVKDLVVPQLISSPAWQEVTE 97
           G R  ED  T  +  G +D +FF V+DG G  +   ++ + ++  ++
Sbjct: 31  GWRVEMEDAHTAVVGIPHGLEDWSFFAVYDGHAGSRVANYCSTHLLEHITTNEDFRAAG- 89

Query: 98  MLRSDVPATEVDEKLPQLLDQAVDDMYKNADNELVKMCEQLNK--------DYASSTSVT 149
                       K   L+ +V+++     +K+ E +       D + ST+V
Sbjct: 90  ------------KSGSALELSVENVKNGIRTGFLKIDEYMRNFSDLRNGMDRSGSTAVG 136

Query: 150 AVLAKGFVAVGHLGDSRIAMGVETPNGLNCEFLTVDHKPDMPHEKLRIMRNGGSVEYLHN 209
           +++ +   + GDSR +    NG  C F T DHKP  P EK RI   GGSV
Sbjct: 137 VMISPKHIYFINCGDSRAVL---YRNGQVC-FSTQDHKPCNPREKERIQNAGGSVMIQRV 192

Query: 210 HNNKPFIRG-GDFSFRKSRGEQPMQLQYSRALGGKDLKMYGLSNQPDVRVVRVTPQHRVM 268
           + +  R GD+ ++  G+ P +           +S +P+V +   +  +
Sbjct: 193 NGSLAVSRALGDYDYKCVDGKGPTEQL--------------VSPEPEVYEILRAEEDEFI 238
```

FIG. 3C

```
Query: 269 ILATDGLWDVMF---AAQAVEIAMQARQEGRNFAQALVEMTLAEQQSRNQSADNITAMTV 325
            ILA DG+WDVM     + V+  ++   + N  +V+ L      S DN++ + V
Sbjct: 239 ILACDGIWDVMSNEELCEYVKSRLEVSDDLENVCNWVVDTCL-----EKGSRDNMSIVLV 293

Query: 326 FF 327
            F
Sbjct: 294 CF 295

>ref|NP_066283.1| protein phosphatase 1A (formerly 2C),
>magnesium-dependent, alpha
            isoform [Homo sapiens]
  ref|XP_007379.1| protein phosphatase 1A (formerly 2C),
magnesium-dependent, alpha
            isoform [Homo sapiens]
            Length = 382

Score = 60.5
bits (145), Expect = 2e-09
 Identities = 63/250 (25%), Positives = 102/250 (40%), Gaps = 43/250 (17%)

Query: 38  GGRKHQEDRFTLCPQLVPGRDDCAFFGVFDGTVGDFASENVKDLVVFQLISSPAWQEVTE 97
            G R   ED  T   L G +  +FF V+DG  G    ++      + ++   + ++   +
Sbjct: 31  GWRVEMEDAHTAVIGLPSGLESWSFFAVYDGHAGSQVAKYCCEHLLDHITNN-------Q 83

Query: 98  MLRSDVFATEVDEKLFQLLDQAVDDMYKNADNELVKMCEQLN-KDYASSTSVTAVLAKGF 156
            +     A V+  +   +  + D   + M E+ +   D + ST+V +++
Sbjct: 84  DFKGSAGAPSVEN-----VKNGIRTGFLEIDEHMRVMSEKKHGADRSGSTAVGVLISPQH 138

Query: 157 VAVGHLGDSRIAMGVETPNGLNCE-----FLTVDHKPDMPHEKLRIMRNGGSVEYLHNHN 211
            +  GDSR         GL C     F T DHKP  P EK RI  GGSV    +
Sbjct: 139 TYFINCGDSR---------GLLCRNRKVHFFTQDHKPSNPLEKERIQNAGGSVMIQRVNG 189

Query: 212 NKPFIRG-GDFSFRKSRGEQPMQLQYSRALGGKDLKMYGLSNQPDVR-VVRVTPQHRVMI 269
            +   R  GDF ++    G+ P +              +S +P+V + R    + +I
Sbjct: 190 SLAVSRALGDFDYKCVHGKGPTEQL---------------VSPEPEVHDIERSEEDDQFII 235

Query: 270 LATDGLWDVM 279
            LA DG+WDVM
Sbjct: 236 LACDGIWDVM 245

>ref|NP_002698.1| protein phosphatase 1G (formerly 2C),
>magnesium-dependent, gamma
            isoform; protein phosphatase 1G (formerly 2C),; protein
            phosphatase 2, catalytic subunit, gamma isoform [Homo
            sapiens]
  ref|XP_002534.1| protein phosphatase 1G (formerly 2C),
magnesium-dependent, gamma
            isoform [Homo sapiens]
            Length = 546

Score = 56.2
bits (134), Expect = 3e-08
 Identities = 50/198 (25%), Positives = 88/198 (44%), Gaps = 30/198 (15%)

Query: 143 ASSTSVTAVLAKGFVAVGHLGDSRIAMGVETPNGLNCEFLTVDHKPDMPHEKLRIMRNGG 202
            + +T+V A++    + V + GDSR  + E    L+ +   DHKP+  E  RI  GG
Sbjct: 327 SGTTAVVALIRGKQLIVANAGDSRCVVS-EAGKALDMSY---DHKPEDEVELARIKNAGG 382

Query: 203 SVEYLHNHNNKPFIRG--GDFSFRKSRGEQPMQLQYSRALGGKDLKMYGLSNQPDVRVVR 260
                 V    N  +    GD ++++     P +                +S PD++V+ +
Sbjct: 383 KVTMDGRVNGGLNLSRAIGDHFYKRNKNLPPEEQM--------------ISALPDIKVLT 428
```

FIG. 3D

```
Query:  261 VTPQHRVMILATDGLWDVMFAAQAVE-IAMQARQEGRNF--------AQALVEMTLAEQQ 311
            +T  H  M++A DG+W+VM + + V+ I   + Q   N          + L++  LA
Sbjct:  429 LTDDHEFMVIACDGIWNVMSSQEVVDFIQSKISQRDENGELRLLESIVEELLDQCLAPDT 488

Query:  312 SRN-QSADNITAMTVFFK 328
            S +    DN+T + + FK
Sbjct:  489 SGDGTGCDNMTCIIICFK 506
```

FIG. 3E

```
VPLPPTSYPAFDAAIFTDIGGRKHQEDRFTLCPQLVPGRDDCAFFGVFDGTVGDFASENV
KDLVVPQLISSPAWQEVTEMLRSDVPATEVDEKLPQLLDQAVDDMYKNADNELVKMCEQL
NKDYASSTSVTAVLAKGFVAVGHLGDSRIAMGVETPNGLNCEFLTVDHKPDMPHEKLRIM
RNGGSVEYLHNHNNKPFIRGGDFSFRKSRGEQPMQLQYSRALGGKDLKMYGLSNQPDVRV
VRVTPQHRVMILATDGLWDVMFAAQAVEIAMQARQEGRNPAQALVEMTLAEQQSRNQSAD
NITAMTV
``` blast of the PP2C protein sequence of Toxoplasma gondii against Plasmodium falciparum genome

```
                                                              Score     E
Sequences producing significant alignments:                   (bits)    Value emb|AL049181.4|PFMAL13P4  Plasmodium falciparum chromosome 1...   71    9e-13
emb|AL133452.1|ATF26O13  Arabidopsis thaliana DNA chromosome...   67    2e-11
emb|AL035475.6|PFMAL4P2  Plasmodium falciparum MAL4P2, compl...   60    3e-09
gb|AF023665.1|AF023665   Plasmodium falciparum protein phosph...  58    1e-08
gb|AC005140.8|AC005140   Plasmodium falciparum chromosome 12 ...  45    5e-05
emb|AL080252.2|ATT12G13  Arabidopsis thaliana DNA chromosome...   43    3e-04
emb|AL161564.2|ATCHRIV64 Arabidopsis thaliana DNA chromosom...    40    0.002
emb|AL049483.1|ATF20B18  Arabidopsis thaliana DNA chromosome...   40    0.002
emb|AL160371.2|LMFLCHR15 Leishmaria major chromosome 15 clo...    37    0.019
emb|AL161584.2|ATCHRIV80 Arabidopsis thaliana DNA chromosom...    34    0.16
gb|AF080447.1|AF080447   Plasmodium chabaudi asparagine-rich ...  28    8.6

Alignments

>emb|AL049181.4|PFMAL13P4 Plasmodium falciparum chromosome 13 strain 3D7,
>*** SEQUENCING IN
            PROGRESS ***, in unordered pieces
         Length = 293431

Score = 71.2 bits (173), Expect = 9e-13
  Identities = 45/161 (27%), Positives = 81/161 (49%), Gaps = 7/161 (4%)
  Frame = +1

Query: 141  DYASSTSVTAVLAKGFVAV----GHLGDSRIAMGVETP--NGLNCEFLTVDHKPDMPHEK 194
            DY S+   ++   F+       H GDSR  MG + P  N +   +T DHKP + EK
Sbjct: 95686 DYNLSGTTCTIILYNFITKKIYSAHTGDSRAVMGKQNPQTNKFSAYNITEDHKPSLKLEK 95865

Query: 195  LRIMRNGGSVEYLHNHNNKPFIRGGDFSFRKS-RGEQPMQLQYSRALGGKDLKMYGLSNQ 253
            +RI+   GG V+  LH        GD ++R   + E    L   SRA+G       G++  +
Sbjct: 95866 DRILAFGGEVKKLH----------GDVAYRVFVKDEMYPGLAMSRAIGDITSSFIGVTCE 96015

Query: 254  PDVRVVRVTPQHRVMILATDGLWDVMFAAQAVEIAMQARQE 294
            P ++++     +  +I+ATDG+W+   +   +  V++   + +++
Sbjct: 96016 PTIKILDKLEEDKFIIVATDGIWEFISSEECVQMVSKKKKK 96138
```

FIG. 3F

```
Score = 71.2 bits (173), Expect = 9e-13
Identities = 45/161 (27%), Positives = 81/161 (49%), Gaps = 7/161 (4%)
Frame = +2

Query: 141   DYASSTSVTAVLAKGFVAV----GHLGDSRIAMGVETP--NGLNCEFLTVDHKPDMPHEK 194
             DY S+  ++ F+       H GDSR MG + P  N +   +T DHKP + EK
Sbjct: 64022 DYNLSGTTCTIILYNFITKKIYSAHTGDSRAVMGKQNPQTNKFSAYNITEDHKPSLKLEK 64201

Query: 195   LRIMRNGGSVEYLHNHNNKPFIRGGDFSFRKS-RGEQPMQLQYSRALGGKDLKMYGLSNQ 253
             RI+  GG V+ LH         GD ++R  + E   L  SRA+G      G++ +
Sbjct: 64202 DRILAFGGEVKKLH---------GDVAYRVFVKDEMYPGLAMSRAIGDITSSFIGVTCE 64351

Query: 254   PDVRVVRVTPQHRVMILATDGLWDVMFAAQAVEIAMQARQE 294
             P ++++   +  +I+ATDG+W+ + + + V++  + +++
Sbjct: 64352 PTIKILDKLEEDKFIIVATDGIWEFISSEECVQMVSKKKKK 64474

>emb|AL133452.1|ATF26O13 Arabidopsis thaliana DNA chromosome 3, BAC clone
>F26O13
            Length = 94349

Score = 66.6 bits (161), Expect = 2e-11
Identities = 57/224 (25%), Positives = 102/224 (45%), Gaps = 5/224 (2%)
Frame = -3

Query: 109   DEKLPQLLDQAVDDMYKNADNELVKMCEQLNKDYASSTSVTAVLAKGFVAVGHLGDSRIA 168
             D+  P   +A  + D+ L     L++  +  +T++TA++     + + GDSR
Sbjct: 44334 DKHFPTSTKKATRSAFVKTDHALAD-ASSLDRS-SGTTALTALILDKTMLIANAGDSRAV 44161

Query: 169   MGVETPNGLNCEFLTVDHKPDMPHEKLRIMRNGGSVEYLHNHNNKPFIRGGDFSFRKSRG 228
             +G    G    E L+ DHKP+    E+LRI + GG +         ++ G
Sbjct: 44160 LG---KRGRAIE-LSKDHKPNCTSERLRIEKLGGVIY-------DGYLNG---------- 44044

Query: 229   EQPMQLQYSRALGGKDLK-----MYGLSNQPDVRVVRVTPQHRVMILATDGLWDVMFAAQ 283
             QL +RALG  +K     + LS +P++    +T +     +I+ DGLWDVM +
Sbjct: 44043 ----QLSVARALGDWHIKGTKGSLCPLSCEPELEEIVLTEEDEYLIMGCDGLWDVMSSQC 43876

Query: 284   AVEIAMQARQEGRNPAQALVEMTLAEQQSRNQSADNITAMTVFF 327
             AV + +  +  +P +    L ++  +   S DN+T + V F
Sbjct: 43875 AVTMVRRELMQHNDPERC--SQALVKEALQRNSCDNLTVVVVCF 43750

Score = 36.2 bits (82), Expect = 0.032
Identities = 21/70 (30%), Positives = 37/70 (52%), Gaps = 1/70 (1%)
Frame = +3

Query: 219   GDFSFRKSR-GEQPMQLQYSRALGGKDLKMYGLSNQPDVRVVRVTPQHRVMILATDGLWD 277
             GD +K+  ++P+  +Y      + K  LS +P +      + PQ + +I A+DGLW+
Sbjct: 17154 GDVYLKKAEFNKEPLYTKYRIR---EPFKRPILSGEPTITEHEIQPQDKFLIFASDGLWE 17324

Query: 278   VMFAAQAVEI 287
             M   +AV+I
Sbjct: 17325 QMSNQEAVDI 17354

>emb|AL035475.6|PFMAL4P2 Plasmodium falciparum MAL4P2, complete sequence
           Length = 234112

Score = 59.7 bits (143), Expect = 3e-09
Identities = 55/222 (24%), Positives = 105/222 (46%), Gaps = 6/222 (2%)
Frame = -3

Query: 116   LDQAVDDMYKNADNELVK----MCEQLNKDYASSTSV-TAVLAKGFVAVGHLGDSRIAMG 170
```

FIG. 3G

```
                    L+ ++    ++  DN L K    + E+ + +Y+S T+    +V+ K   + V ++GDSR   +
Sbjct: 130904  LENSLKYSFQEIDNYLCKNIINIKEENHSNYSSGTTACVSVIFKNMLYVANIGDSRCII-
130728

Query:    171  VETPNGLNCEFLTVDHKPDM-PHEKLRIMRNGGSVEYLHNHNNKPFIRGGDFSFRKSRGE  229
                 + NG     LTVDH+  +    E+ RI+++GG ++          + G  SF K    E
Sbjct: 130727  --SKNG-RAIVLTVDHRASINKKEQDRILKSGGILDDEGYLGGCLGVCRGFGSFHKKTKE
130557

Query:    230  QPMQLQYSRALGGKDLKMYGLSNQPDVRVVRVTPQHRVMILATDGLWDVMFAAQAVEIAM  289
                              K+ GL  +PD+  +++T      +I+    DG++DV+ +  +AV
Sbjct: 130556  ----------------KLKGLICEPDLFHIKLTDDDEFLIICCDGIFDVITSQEAVNTVK
-130425

Query:    290  QARQEGRNPAQALVEMTLAEQQSRNQSADNITAMTVFFKKTD 331
                +  + R+   A    L +    + +S DN++ + V F+   D
Sbjct: 130424  NSLIQSRDAKTA--AEALCQLAYKKKSLDNLSVLVVIFQNPD 130305

>gb|AF023665.1|AF023665 Plasmodium falciparum protein phosphatase 2c mRNA,
>complete cds
            Length = 3508

Score =  57.8 bits (138), Expect = 1e-08
 Identities = 61/213 (28%), Positives = 93/213 (43%), Gaps = 32/213 (15%)
 Frame = +1

Query:     97  EMLRSDVPATEVDEKLPQLLDQAV---------DDMYKNADNEL-------VKMCEQL--  138
               E+   SD+     DE  ++D +         DD  N D E       V    E+L
Sbjct:   2029  EVNNSDIERLAYDEASANVIDNNINNDIHEEDEDDENNNNDEETGEDDCNGVYSSEELRL  2208

Query:    139  -----NKDY-------ASSTSVTAVLAKGFVAVGHLGDSRIAMGVETPNGLNCEFLTVDH  186
                    + DY         ST++ AV+ KG++ V + GDSR    +  NG N   ++ DH
Sbjct:   2209  FENYYSNDYEDNIAYSCGSTALVAVILKGYLIVANAGDSR---AIVCFNG-NSLGMSTDH  2376

Query:    187  KPDMPHEKLRIMRNGGSVEYLHNHNNKPFIRGGDFSFRKSRGEQPMQLQYSRA--LGGKD  244
               KP +   E+ RI + GG    Y+  N       G+ +  ++ G+       L Y R    L KD
Sbjct:   2377  KPHLQTEEARIKKAGG---YIANGRVD-----GNLNLTRAIGD----LHYKRDPFLPQKD  2520

Query:    245  LKMYGLSNQPDVRVVRVTPQHRVMILATDGLWD 277
                K   +S P++  V +TP+  +  LA DG+WD
Sbjct:   2521  QK---ISAFPEITCVTLTPEDEFLFLACDGIWD 2610

>gb|AC005140.8|AC005140 Plasmodium falciparum chromosome 12 clone 3D7, ***
>SEQUENCING IN PROGRESS
            ***, 4 unordered pieces
            Length = 310779

Score =  45.4 bits (106), Expect = 5e-05
 Identities = 39/154 (25%), Positives = 75/154 (48%), Gaps = 8/154 (5%)
 Frame = -2

Query:    182  LTVDHKPDMPHEKLRIMRNGGSVEYLHNHN-----NKPFIRGGDFSFRKSRGEQPMQLQY  236
               L++ HKPD+  E++RI++ GG  +    N       +K        + + KS+ +  + L
Sbjct: 271322  LSLRHKPDLQEERIRILKCGGIIANINGINRIITKHKDRNNLNENNNNKSKEKTFLALST
271143

Query:    237  SRALGGKDLKMYG--LSNQPDVRVVRVT-PQHRVMILATDGLWDVMFAAQAVEIAMQARQ  293
               SR+  G   K+    + +P + V +        ++LATDG +V+  +   ++I      +
Sbjct: 271142  SRSFGDISYKIPRKIVQCKPFISVYTIDFDLDSFLVLATDGILNVLSDEEIIDIIW--KN
270969
```

FIG. 3H

```
Query: 294    EGRNPAQALVEMTLAEQQSRNQSADNITAMTVFF 327
              R P QA  E  +· + +R  S D+ T  -+FF
Sbjct: 270968 IHRKPEQAAEE--VVNEATRRGSTDDKTCTVIFF 270873

>gb|AF080447.1|AF080447 Plasmodium chabaudi asparagine-rich protein gene,
>partial cds
          Length = 3948

Score = 28.1 bits (61), Expect = 8.6
 Identities = 19/68 (27%), Positives = 32/68 (46%), Gaps. = 5/68 (7%)
 Frame = -3

Query: 121  DDMYKNADNELVKMCE-----QLNKDYASSTSVTAVLAKGFVAVGHLGDSRIAMGVETPN 175
            DD  K +   L+  C+       Q+NKD    + TA+  KG++   +  S+     V T N
Sbjct: 763  DDKTKKSTKNLINPCKFNESIQINKDINFCNNKTAIDQKGYINQKYTNKSK---NVFTKN 593

Query: 176  GLNCEFLT 183
             ++ + LT
Sbjct: 592  QISTKLLT 569
```

SEQUENCE LISTING

<160> NUMBER OF SEQ ID NOS: 19

<210> SEQ ID NO 1
<211> LENGTH: 996
<212> TYPE: DNA
<213> ORGANISM: Toxoplasma gondii
<220> FEATURE:
<221> NAME/KEY: CDS
<222> LOCATION: (1)..(996)
<223> OTHER INFORMATION:

<400> SEQUENCE: 1

```
atg aag tcc tct gct gaa att agg cgg acc atg gat gtc cct cct acc        48
Met Lys Ser Ser Ala Glu Ile Arg Arg Thr Met Asp Val Pro Pro Thr
1               5                   10                  15 att cat gta cct ctc cct cca acg tcg tat ccc gct ttc gat gct gcg        96
Ile His Val Pro Leu Pro Pro Thr Ser Tyr Pro Ala Phe Asp Ala Ala
            20                  25                  30 atc ttc aca gac atc ggt ggg cgc aag cat cag gaa gat agg ttc act       144
Ile Phe Thr Asp Ile Gly Gly Arg Lys His Gln Glu Asp Arg Phe Thr
        35                  40                  45 ctc tgt ccg cag ctc gtt ccc ggc cga gac gac tgc gcc ttc ttc ggt       192
Leu Cys Pro Gln Leu Val Pro Gly Arg Asp Asp Cys Ala Phe Phe Gly
    50                  55                  60 gtc ttc gat ggc act gtt gga gat ttc gcc agc gaa aat gtg aag gat       240
Val Phe Asp Gly Thr Val Gly Asp Phe Ala Ser Glu Asn Val Lys Asp
65                  70                  75                  80 ctt gtt gtt cca cag ttg att tcc tcg ccc gcg tgg cag gag gtg act       288
Leu Val Val Pro Gln Leu Ile Ser Ser Pro Ala Trp Gln Glu Val Thr
                85                  90                  95 gag atg ctg aga tca gac gta ccc gcc acc gag gtg gac gag aag ctc       336
Glu Met Leu Arg Ser Asp Val Pro Ala Thr Glu Val Asp Glu Lys Leu
            100                 105                 110 cct cag ttg ctt gat cag gca gtc gat gac atg tac aag aac gca gac       384
Pro Gln Leu Leu Asp Gln Ala Val Asp Asp Met Tyr Lys Asn Ala Asp
        115                 120                 125 aac gaa ctt gtg aag atg tgc gag cag ctt aac aaa gac tac gcg agc       432
Asn Glu Leu Val Lys Met Cys Glu Gln Leu Asn Lys Asp Tyr Ala Ser
    130                 135                 140 agc acc tcc gtc acg gca gtc ttg gcc aaa ggc ttc gtg gct gtt ggt       480
Ser Thr Ser Val Thr Ala Val Leu Ala Lys Gly Phe Val Ala Val Gly
145                 150                 155                 160 cat ctg ggc gac agc cgc atc gct atg gga gtc gag acg ccg aac ggg       528
His Leu Gly Asp Ser Arg Ile Ala Met Gly Val Glu Thr Pro Asn Gly
                165                 170                 175
```

```
ttg aac tgc gag ttc ttg acc gtt gac cac aag ccg gat atg cca cat    576
Leu Asn Cys Glu Phe Leu Thr Val Asp His Lys Pro Asp Met Pro His
            180                 185                 190 gag aaa ctg cgc atc atg cgc aat gga ggc agt gtt gag tat ctc cac    624
Glu Lys Leu Arg Ile Met Arg Asn Gly Gly Ser Val Glu Tyr Leu His
        195                 200                 205 aac cac aac aac aaa ccg ttc att cga ggt ggt gac ttc tcg ttc cgg    672
Asn His Asn Asn Lys Pro Phe Ile Arg Gly Gly Asp Phe Ser Phe Arg
210                 215                 220 aag tcg cgc gga gag cag ccg atg cag ctc cag tac tcc cga gct ttg    720
Lys Ser Arg Gly Glu Gln Pro Met Gln Leu Gln Tyr Ser Arg Ala Leu
225                 230                 235                 240 ggc ggg aag gac ctg aag atg tac ggt ttg agc aac caa ccc gac gta    768
Gly Gly Lys Asp Leu Lys Met Tyr Gly Leu Ser Asn Gln Pro Asp Val
            245                 250                 255 cgc gtt gtc cgc gtc acg cct caa cac cga gtg atg att ctc gcg act    816
Arg Val Val Arg Val Thr Pro Gln His Arg Val Met Ile Leu Ala Thr
        260                 265                 270 gat ggc ttg tgg gac gtc atg ttt gcg gcg caa gct gta gag atc gct    864
Asp Gly Leu Trp Asp Val Met Phe Ala Ala Gln Ala Val Glu Ile Ala
    275                 280                 285 atg cag gcc cga cag gaa gga agg aac cca gcg cag gcg ctg gtg gag    912
Met Gln Ala Arg Gln Glu Gly Arg Asn Pro Ala Gln Ala Leu Val Glu
290                 295                 300 atg acc ctc gct gag cag cag agc cgc aac caa agt gca gac aac att    960
Met Thr Leu Ala Glu Gln Gln Ser Arg Asn Gln Ser Ala Asp Asn Ile
305                 310                 315                 320 act gcg atg aca gtg ttc ttc aag aag act gat tag                    996
Thr Ala Met Thr Val Phe Phe Lys Lys Thr Asp
            325                 330

<210> SEQ ID NO 2
<211> LENGTH: 331
<212> TYPE: PRT
<213> ORGANISM: Toxoplasma gondii

<400> SEQUENCE: 2

Met Lys Ser Ser Ala Glu Ile Arg Arg Thr Met Asp Val Pro Pro Thr
1               5                   10                  15

Ile His Val Pro Leu Pro Pro Thr Ser Tyr Pro Ala Phe Asp Ala Ala
            20                  25                  30

Ile Phe Thr Asp Ile Gly Gly Arg Lys His Gln Glu Asp Arg Phe Thr
        35                  40                  45

Leu Cys Pro Gln Leu Val Pro Gly Arg Asp Asp Cys Ala Phe Phe Gly
    50                  55                  60

Val Phe Asp Gly Thr Val Gly Asp Phe Ala Ser Glu Asn Val Lys Asp
65                  70                  75                  80

Leu Val Val Pro Gln Leu Ile Ser Ser Pro Ala Trp Gln Glu Val Thr
                85                  90                  95

Glu Met Leu Arg Ser Asp Val Pro Ala Thr Glu Val Asp Glu Lys Leu
            100                 105                 110

Pro Gln Leu Leu Asp Gln Ala Val Asp Asp Met Tyr Lys Asn Ala Asp
        115                 120                 125

Asn Glu Leu Val Lys Met Cys Glu Gln Leu Asn Lys Asp Tyr Ala Ser
    130                 135                 140

Ser Thr Ser Val Thr Ala Val Leu Ala Lys Gly Phe Val Ala Val Gly
145                 150                 155                 160
```

-continued

His Leu Gly Asp Ser Arg Ile Ala Met Gly Val Glu Thr Pro Asn Gly
                165                 170                 175

Leu Asn Cys Glu Phe Leu Thr Val Asp His Lys Pro Asp Met Pro His
            180                 185                 190

Glu Lys Leu Arg Ile Met Arg Asn Gly Gly Ser Val Glu Tyr Leu His
        195                 200                 205

Asn His Asn Asn Lys Pro Phe Ile Arg Gly Gly Asp Phe Ser Phe Arg
    210                 215                 220

Lys Ser Arg Gly Glu Gln Pro Met Gln Leu Gln Tyr Ser Arg Ala Leu
225                 230                 235                 240

Gly Gly Lys Asp Leu Lys Met Tyr Gly Leu Ser Asn Gln Pro Asp Val
                245                 250                 255

Arg Val Val Arg Val Thr Pro Gln His Arg Val Met Ile Leu Ala Thr
            260                 265                 270

Asp Gly Leu Trp Asp Val Met Phe Ala Ala Gln Ala Val Glu Ile Ala
        275                 280                 285

Met Gln Ala Arg Gln Glu Gly Arg Asn Pro Ala Gln Ala Leu Val Glu
    290                 295                 300

Met Thr Leu Ala Glu Gln Gln Ser Arg Asn Gln Ser Ala Asp Asn Ile
305                 310                 315                 320

Thr Ala Met Thr Val Phe Phe Lys Lys Thr Asp
                325                 330

<210> SEQ ID NO 3
<211> LENGTH: 248
<212> TYPE: PRT
<213> ORGANISM: Homo sapiens

<400> SEQUENCE: 3

Leu Ile Thr Arg Val Ser Tyr Phe Ala Val Phe Asp Gly His Gly Gly
1               5                   10                  15

Ile Arg Ala Ser Lys Phe Ala Ala Gln Asn Leu His Gln Asn Leu Ile
            20                  25                  30

Arg Lys Phe Pro Lys Gly Asp Val Ile Ser Val Glu Lys Thr Val Lys
        35                  40                  45

Arg Cys Leu Leu Asp Thr Phe Lys His Thr Asp Glu Glu Phe Leu Lys
    50                  55                  60

Gln Ala Ser Ser Gln Lys Pro Ala Trp Lys Asp Gly Ser Thr Ala Thr
65                  70                  75                  80

Cys Val Leu Ala Val Asp Asn Ile Leu Tyr Ile Ala Asn Leu Gly Asp
                85                  90                  95

Ser Arg Ala Ile Leu Cys Arg Tyr Asn Glu Glu Ser Gln Lys His Ala
            100                 105                 110

Ala Leu Ser Leu Ser Lys Glu His Asn Pro Thr Gln Tyr Glu Glu Arg
        115                 120                 125

Met Arg Ile Gln Lys Ala Gly Gly Asn Val Arg Asp Gly Arg Val Leu
    130                 135                 140

Gly Val Leu Glu Val Ser Arg Ser Ile Gly Asp Gly Gln Tyr Lys Arg
145                 150                 155                 160

Cys Gly Val Thr Ser Val Pro Asp Ile Arg Arg Cys Gln Leu Thr Pro
                165                 170                 175

Asn Asp Arg Phe Ile Leu Leu Ala Cys Asp Gly Leu Phe Lys Val Phe
            180                 185                 190

Thr Pro Glu Glu Ala Val Asn Phe Ile Leu Ser Cys Leu Glu Asp Glu
        195                 200                 205

```
Lys Ile Gln Thr Arg Glu Gly Lys Ser Ala Ala Asp Ala Arg Tyr Glu
            210                 215                 220

Ala Ala Cys Asn Arg Leu Ala Asn Lys Ala Val Gln Arg Gly Ser Ala
225                 230                 235                 240

Asp Asn Val Thr Val Met Val Val
                245

<210> SEQ ID NO 4
<211> LENGTH: 265
<212> TYPE: PRT
<213> ORGANISM: Homo sapiens

<400> SEQUENCE: 4

Gly Trp Arg Val Glu Met Glu Asp Ala His Thr Ala Val Val Gly Ile
1               5                   10                  15

Pro His Gly Leu Glu Asp Trp Ser Phe Phe Ala Val Tyr Asp Gly His
            20                  25                  30

Ala Gly Ser Arg Val Ala Asn Tyr Cys Ser Thr His Leu Leu Glu His
        35                  40                  45

Ile Thr Thr Asn Glu Asp Phe Arg Ala Ala Gly Lys Ser Gly Ser Ala
    50                  55                  60

Leu Glu Leu Ser Val Glu Asn Val Lys Asn Gly Ile Arg Thr Gly Phe
65                  70                  75                  80

Leu Lys Ile Asp Glu Tyr Met Arg Asn Phe Ser Asp Leu Arg Asn Gly
                85                  90                  95

Met Asp Arg Ser Gly Ser Thr Ala Val Gly Val Met Ile Ser Pro Lys
            100                 105                 110

His Ile Tyr Phe Ile Asn Cys Gly Asp Ser Arg Ala Val Leu Tyr Arg
        115                 120                 125

Asn Gly Gln Val Cys Phe Ser Thr Gln Asp His Lys Pro Cys Asn Pro
    130                 135                 140

Arg Glu Lys Glu Arg Ile Gln Asn Ala Gly Gly Ser Val Met Ile Gln
145                 150                 155                 160

Arg Val Asn Gly Ser Leu Ala Val Ser Arg Ala Leu Gly Asp Tyr Asp
                165                 170                 175

Tyr Lys Cys Val Asp Gly Lys Gly Pro Thr Glu Gln Leu Val Ser Pro
            180                 185                 190

Glu Pro Glu Val Tyr Glu Ile Leu Arg Ala Glu Glu Asp Glu Phe Ile
        195                 200                 205

Ile Leu Ala Cys Asp Gly Ile Trp Asp Val Met Ser Asn Glu Glu Leu
    210                 215                 220

Cys Glu Tyr Val Lys Ser Arg Leu Glu Val Ser Asp Asp Leu Glu Asn
225                 230                 235                 240

Val Cys Asn Trp Val Val Asp Thr Cys Leu His Lys Gly Ser Arg Asp
                245                 250                 255

Asn Met Ser Ile Val Leu Val Cys Phe
            260                 265

<210> SEQ ID NO 5
<211> LENGTH: 186
<212> TYPE: PRT
<213> ORGANISM: Homo sapiens

<400> SEQUENCE: 5

Glu Glu Pro Gly Ser Asp Ser Gly Thr Thr Ala Val Val Ala Leu Ile
1               5                   10                  15
```

```
Arg Gly Lys Gln Leu Ile Val Ala Asn Ala Gly Asp Ser Arg Cys Val
            20                  25                  30

Val Ser Glu Ala Gly Lys Ala Leu Asp Met Ser Tyr Asp His Lys Pro
        35                  40                  45

Glu Asp Glu Val Glu Leu Ala Arg Ile Lys Asn Ala Gly Gly Lys Val
    50                  55                  60

Thr Met Asp Gly Arg Val Asn Gly Gly Leu Asn Leu Ser Arg Ala Ile
65                  70                  75                  80

Gly Asp His Phe Tyr Lys Arg Asn Lys Asn Leu Pro Pro Glu Glu Gln
                85                  90                  95

Met Ile Ser Ala Leu Pro Asp Ile Lys Val Leu Thr Leu Thr Asp Asp
            100                 105                 110

His Glu Phe Met Val Ile Ala Cys Asp Gly Ile Trp Asn Val Met Ser
        115                 120                 125

Ser Gln Glu Val Val Asp Phe Ile Gln Ser Lys Ile Ser Gln Arg Asp
    130                 135                 140

Glu Asn Gly Glu Leu Arg Leu Leu Ser Ser Ile Val Glu Glu Leu Leu
145                 150                 155                 160

Asp Gln Cys Leu Ala Pro Asp Thr Ser Gly Asp Gly Thr Cys Asp
                165                 170                 175

Asn Met Thr Cys Ile Ile Cys Phe Lys
            180                 185

<210> SEQ ID NO 6
<211> LENGTH: 151
<212> TYPE: PRT
<213> ORGANISM: Plasmodium falciparum

<400> SEQUENCE: 6

Asp Tyr Asn Leu Ser Gly Thr Thr Cys Thr Ile Ile Leu Tyr Asn Phe
1               5                   10                  15

Ile Thr Lys Lys Ile Tyr Ser Ala His Thr Gly Asp Ser Arg Ala Val
            20                  25                  30

Met Gly Lys Gln Asn Pro Gln Thr Asn Lys Phe Asp Ala Tyr Asn Ile
        35                  40                  45

Thr Glu Asp His Lys Pro Ser Leu Lys Leu Glu Lys Asp Arg Ile Leu
    50                  55                  60

Ala Phe Gly Gly Glu Val Lys Lys Leu His Gly Asp Val Ala Tyr Arg
65                  70                  75                  80

Val Phe Val Lys Asp Glu Met Tyr Pro Gly Leu Ala Met Ser Arg Ala
                85                  90                  95

Ile Gly Asp Ile Thr Ser Ser Phe Ile Gly Val Thr Cys Glu Pro Thr
            100                 105                 110

Ile Lys Ile Leu Asp Lys Leu Glu Asp Lys Phe Ile Ile Val Ala
        115                 120                 125

Thr Asp Gly Ile Trp Glu Phe Ile Ser Ser Glu Glu Cys Val Gln Met
    130                 135                 140

Val Ser Lys Lys Lys Lys Lys
145                 150

<210> SEQ ID NO 7
<211> LENGTH: 150
<212> TYPE: PRT
<213> ORGANISM: Plasmodium falciparum

<400> SEQUENCE: 7
```

```
Asp Tyr Asn Leu Ser Gly Thr Thr Cys Thr Ile Ile Leu Tyr Asn Phe
1               5                   10                  15

Ile Thr Lys Lys Ile Tyr Ser Ala His Thr Gly Asp Ser Arg Ala Val
            20                  25                  30

Met Gly Lys Gln Asn Pro Gln Thr Asn Lys Phe Ser Ala Tyr Asn Ile
        35                  40                  45

Thr Glu Asp His Lys Pro Ser Leu Lys Leu Glu Lys Asp Arg Ile Leu
    50                  55                  60

Ala Phe Gly Gly Glu Val Gly Gly Leu His Gly Asp Val Ala Tyr Arg
65              70                  75                  80

Val Phe Val Lys Asp Glu Met Tyr Pro Gly Leu Ala Met Ser Arg Ala
            85                  90                  95

Ile Gly Asp Ile Thr Ser Ser Phe Ile Gly Val Thr Cys Glu Pro Thr
            100                 105                 110

Ile Lys Ile Leu Asp Lys Leu Glu Glu Asp Lys Phe Ile Ile Val Ala
            115                 120                 125

Thr Asp Gly Ile Trp Glu Phe Ile Ser Ser Glu Glu Cys Val Gln Met
    130                 135                 140

Val Ser Lys Lys Lys
145             150

<210> SEQ ID NO 8
<211> LENGTH: 196
<212> TYPE: PRT
<213> ORGANISM: Plasmodium falciparum

<400> SEQUENCE: 8

Asp Lys His Phe Pro Thr Ser Thr Lys Lys Ala Thr Arg Ser Ala Phe
1               5                   10                  15

Val Lys Thr Asp His Ala Leu Ala Asp Ala Ser Ser Leu Asp Arg Ser
            20                  25                  30

Ser Gly Thr Thr Ala Leu Thr Ala Leu Ile Leu Asp Lys Thr Met Leu
        35                  40                  45

Ile Ala Asn Ala Gly Asp Ser Arg Ala Val Leu Gly Lys Arg Lys Arg
50                  55                  60

Ala Ile Glu Leu Ser Lys Asp His Lys Pro Asn Cys Thr Ser Glu Arg
65              70                  75                  80

Leu Arg Ile Glu Lys Leu Gly Gly Val Ile Tyr Asp Gly Tyr Leu Asn
            85                  90                  95

Gly Gln Leu Ser Val Ala Arg Arg Ala Leu Gly Asp Trp His Ile Lys
            100                 105                 110

Gly Thr Lys Gly Ser Leu Cys Pro Leu Ser Cys Glu Pro Glu Leu Glu
            115                 120                 125

Glu Ile Val Leu Thr Glu Glu Asp Glu Tyr Leu Ile Met Gly Cys Asp
    130                 135                 140

Gly Leu Trp Asp Val Met Ser Ser Gln Cys Ala Val Thr Met Val Arg
145                 150                 155                 160

Arg Glu Leu Met Gln His Asn Asp Pro Glu Arg Cys Ser Gln Ala Leu
                165                 170                 175

Val Lys Glu Ala Leu Gln Arg Asn Ser Cys Asp Asn Leu Thr Val Val
            180                 185                 190

Val Val Cys Phe
            195
```

<210> SEQ ID NO 9
<211> LENGTH: 67
<212> TYPE: PRT
<213> ORGANISM: Arabidopsis thaliana

<400> SEQUENCE: 9

Gly Asp Val Tyr Leu Lys Lys Ala Glu Phe Asn Lys Glu Pro Leu Tyr
1               5                   10                  15

Thr Lys Tyr Arg Ile Arg Glu Pro Phe Lys Arg Pro Ile Leu Ser Gly
            20                  25                  30

Glu Pro Thr Ile Thr Glu His Glu Ile Gln Pro Gln Asp Lys Phe Leu
        35                  40                  45

Ile Phe Ala Ser Asp Gly Leu Trp Glu Gln Met Ser Asn Gln Glu Ala
    50                  55                  60

Val Asp Ile
65

<210> SEQ ID NO 10
<211> LENGTH: 200
<212> TYPE: PRT
<213> ORGANISM: Plasmodium falciparum

<400> SEQUENCE: 10

Leu Glu Asn Ser Leu Lys Tyr Ser Phe Gln Glu Ile Asp Asn Tyr Leu
1               5                   10                  15

Cys Lys Asn Ile Ile Asn Ile Lys Glu Glu Asn His Ser Asn Tyr Ser
            20                  25                  30

Ser Gly Thr Thr Ala Cys Val Ser Val Ile Phe Lys Asn Met Leu Tyr
        35                  40                  45

Val Ala Asn Ile Gly Asp Ser Arg Cys Ile Ile Ser Lys Asn Gly Arg
    50                  55                  60

Ala Ile Val Leu Thr Val Asp His Arg Ala Ser Ile Asn Lys Lys Glu
65                  70                  75                  80

Gln Asp Arg Ile Leu Lys Ser Gly Gly Ile Leu Asp Asp Glu Gly Tyr
                85                  90                  95

Leu Gly Gly Cys Leu Gly Val Cys Arg Gly Phe Gly Ser Phe His Lys
            100                 105                 110

Lys Thr Lys Glu Lys Leu Lys Gly Leu Ile Cys Glu Pro Asp Leu Phe
        115                 120                 125

His Ile Lys Leu Thr Asp Asp Asp Glu Phe Leu Ile Ile Cys Cys Asp
    130                 135                 140

Gly Ile Phe Asp Val Ile Thr Ser Gln Glu Ala Val Asn Thr Val Lys
145                 150                 155                 160

Asn Ser Leu Ile Gln Ser Arg Asp Ala Lys Thr Ala Ala Glu Ala Leu
                165                 170                 175

Cys Gln Leu Ala Tyr Lys Lys Ser Leu Asp Asn Leu Ser Val Leu
            180                 185                 190

Val Val Ile Phe Gln Asn Pro Asp
        195                 200

<210> SEQ ID NO 11
<211> LENGTH: 232
<212> TYPE: PRT
<213> ORGANISM: Plasmodium falciparum

<400> SEQUENCE: 11

Asn Asp Asn Thr Asn Gly Asn Ile Asn Ser Tyr Thr Asn Asp Asp Ile
1               5                   10                  15

His Asn Asn Gly Ser Leu Gln Gly Tyr Glu Gln Asp Gly Leu Ile Gln
                20                  25                  30

Asn Arg Asn Asn Gly Asp Glu Val Asn Asn Ser Asp Ile Glu Arg Leu
            35                  40                  45

Ala Tyr Asp Glu Ala Ser Ala Asn Val Ile Asp Asn Asn Ile Asn Asn
        50                  55                  60

Asp Ile His Glu Glu Asp Glu Asp Glu Asn Asn Asn Asn Asn Asp Glu
65                  70                  75                  80

Glu Thr Gly Glu Asp Asp Cys Asn Gly Val Tyr Ser Ser Glu Glu Leu
                85                  90                  95

Arg Leu Phe Glu Asn Tyr Tyr Ser Asn Asp Tyr Glu Asp Asn Ile Ala
            100                 105                 110

Tyr Ser Cys Gly Ser Thr Ala Leu Val Ala Val Ile Leu Lys Gly Tyr
        115                 120                 125

Leu Ile Val Ala Asn Ala Gly Asp Ser Arg Ala Ile Val Cys Phe Asn
130                 135                 140

Gly Asn Ser Leu Gly Met Ser Thr Asp His Lys Pro His Leu Gln Thr
145                 150                 155                 160

Glu Glu Ala Arg Ile Lys Lys Ala Gly Gly Tyr Ile Ala Asn Gly Arg
                165                 170                 175

Val Asp Gly Asn Leu Asn Leu Thr Arg Ala Ile Gly Asp Leu His Tyr
            180                 185                 190

Lys Arg Asp Pro Phe Leu Pro Gln Lys Asp Gln Lys Ile Ser Ala Phe
        195                 200                 205

Pro Glu Ile Thr Cys Val Thr Leu Thr Pro Glu Asp Glu Phe Leu Phe
    210                 215                 220

Leu Ala Cys Asp Gly Ile Trp Asp
225                 230

<210> SEQ ID NO 12
<211> LENGTH: 150
<212> TYPE: PRT
<213> ORGANISM: Plasmodium falciparum

<400> SEQUENCE: 12

Leu Ser Leu Arg His Lys Pro Asp Leu Gln Glu Glu Arg Ile Arg Ile
1               5                   10                  15

Leu Lys Cys Gly Gly Ile Ile Ala Asn Ile Asn Gly Ile Asn Arg Ile
            20                  25                  30

Thr Lys His Lys Asp Arg Asn Asn Leu Asn Glu Asn Asn Asn Asn Lys
        35                  40                  45

Ser Lys Glu Lys Thr Phe Leu Ala Leu Ser Thr Ser Arg Ser Phe Gly
    50                  55                  60

Asp Ile Ser Tyr Lys Ile Pro Arg Lys Ile Val Gln Cys Lys Pro Phe
65                  70                  75                  80

Ile Ser Val Tyr Thr Ile Asp Phe Asp Leu Asp Ser Phe Leu Val Leu
                85                  90                  95

Ala Thr Asp Gly Gly Ile Leu Asn Val Leu Ser Asp Glu Glu Ile Ile
            100                 105                 110

Asp Ile Ile Trp Lys Asn Ile His Arg Lys Pro Glu Gln Ala Ala Glu
        115                 120                 125

Glu Val Val Asn Glu Ala Thr Arg Arg Gly Ser Thr Asp Asp Lys Thr
    130                 135                 140

Cys Thr Val Ile Phe Phe

-continued

```
145                 150

<210> SEQ ID NO 13
<211> LENGTH: 87
<212> TYPE: PRT
<213> ORGANISM: Plasmodium chabaudi

<400> SEQUENCE: 13

Met Asp Lys His Ile Ser Asp Met Leu Tyr Ala Tyr Asn His Asn Asn
1               5                   10                  15

Val Ser Met Ser Phe Glu Asp Asp Lys Thr Lys Ser Thr Lys Asn
            20                  25                  30

Leu Ile Asn Pro Cys Lys Phe Asn Glu Ser Ile Gln Ile Asn Lys Asp
        35                  40                  45

Ile Asn Phe Cys Asn Asn Lys Thr Ala Ile Asp Gln Lys Gly Tyr Ile
    50                  55                  60

Asn Gln Lys Tyr Thr Asn Lys Ser Lys Asn Val Phe Thr Lys Asn Gln
65                  70                  75                  80

Ile Ser Thr Lys Leu Leu Thr
                85

<210> SEQ ID NO 14
<211> LENGTH: 15
<212> TYPE: PRT
<213> ORGANISM: Toxoplasma gondii

<400> SEQUENCE: 14

Ser Val Phe Asp Gly Thr Val Gly Asp Phe Ala Gln Glu Asn Val
1               5                   10                  15

<210> SEQ ID NO 15
<211> LENGTH: 15
<212> TYPE: PRT
<213> ORGANISM: Toxoplasma gondii

<400> SEQUENCE: 15

Asn Gln Ser Ala Asp Asn Ile Thr Ala Met Thr Val Phe Phe Lys
1               5                   10                  15

<210> SEQ ID NO 16
<211> LENGTH: 24
<212> TYPE: DNA
<213> ORGANISM: Artificial Sequence
<220> FEATURE:
<223> OTHER INFORMATION: synthetic DNA

<400> SEQUENCE: 16
agtgcagaca acattactgc gatg                                      24

<210> SEQ ID NO 17
<211> LENGTH: 21
<212> TYPE: DNA
<213> ORGANISM: Artificial Sequence
<220> FEATURE:
<223> OTHER INFORMATION: synthetic DNA

<400> SEQUENCE: 17
agacacacca agaatctcgt c                                         21

<210> SEQ ID NO 18
<211> LENGTH: 34
<212> TYPE: DNA
<213> ORGANISM: Artificial Sequence
```

-continued

```
<220> FEATURE:
<223> OTHER INFORMATION: synthetic DNA

<400> SEQUENCE: 18
gccgaattcc catgaagtcc tctgctgaaa ttag                    34

<210> SEQ ID NO 19
<211> LENGTH: 34
<212> TYPE: DNA
<213> ORGANISM: Artificial Sequence
<220> FEATURE:
<223> OTHER INFORMATION: synthetic DNA

<400> SEQUENCE: 19
gcctcagact aatcagtctt cttgaagaac actg                    34
```

US 6,949,352 B2

SERINE-THREONINE PHOSPHATASE PROTEIN OF A PARASITIC ORGANISM OF THE APICOMPLEXA PHYLUM, APPLICATIONS IN THERAPEUTICS

This application claims the benefit of provisional application No. 60/291,609 filed May 18, 2001.

FIELD OF THE INVENTION

The invention is directed to a new serine-threonine phosphatase protein of a parasitic organism of the Apicomplexa phylum and fragments thereof. More particularly, this invention is directed an active molecule capable of modulating the activity of such a protein. Furthermore, this invention is directed to uses of this protein for screening molecules capable of modulating the activity of a serine-threonine phosphatase protein of a parasitic organism of the Apicomplexa phylum, as well as for methods for preventing and treating parasitic infections.

BACKGROUND OF THE INVENTION

Protozoan parasites such as *Plasmodium falciparum* and *Toxoplasma gondii* belong to the phylum of *Apicomplexa* and the class of Coccidia.

Coccidia are among the most important parasites of animals parasites and some are human pathogens of major medical importance: the causative agent of malaria, *Plasmodium falciparum*, causes death of more than two million children every year while other Apicomplexa such as *Toxoplasma gondii* and to a lesser extent *Cryptosporidium parvum* are devastating human pathogens when they parasitize immunocompromised hosts.

As to *Toxoplasma gondii*, following an asymptomatic parasitic process caused by the tachyzoite stage (replicative stage) but efficiently controlled by the host immune system, the parasite may persist as cryptic, <<dormant>> bradyzoite stage within intracellular cysts. These cysts resulting from host and parasite factors preferentially develop in muscle and brain tissues. Though the mechanisms by which cysts persist in the brain are not well defined yet, it is clear that the immune cells and their associated cytokine production play a major role. When this subtle immune interplay is disrupted as it occurs in AIDS patients, it induces cyst reactivation which is accompanied by the parasite differentiation from the slow growing bradyzoite stage into a highly replicative tachyzoite stage responsible for infiltrated <<inflammatory>> foci that leads to encephalitis. Currently existing chemotherapeutic treatments, while effective at controlling the parasite are poorly tolerated particularly by immunocompromised individuals.

Toxoplasma infection may also be congenitally acquired. Such infection occurs only when a woman becomes primo-infected during pregnancy and severity of the disease may depend upon the stage of pregnancy at time of infection. Focal lesions develop in the placenta and the fetus may become infected. Apart from abortion, by far the most common sequel of congenital toxoplasmosis is ocular disease (blindness) but mental retardation is also quite common.

As such the identification of molecules or molecular complexes of parasite origin and involved in the survival of the parasite should remain a research priority since it could lead to more targeted treatments.

Certain developmental stages of these parasites including the sporozoites of *Plasmodium, Cryptosporidium* and *Toxoplasma* as well as the tachyzoites of *Toxoplasma*, move by a gliding motion across either a mucous layer or an extracellular matrix before encountering their host cells. They subsequently enter these cells by an active process and once in a suitable intracellular niche, they either multiply and/or differentiate, two steps required for parasite spreading before transmission to a new host.

The strategies selected by these parasites for either gliding onto a substratum or for invading their host cells depend on the dynamics of their actin cytoskeleton. However, unlike during the crawling motility of higher eucaryotes, the remodeling of actin cytoskeleton remains discrete and speed values of gliding zoïtes are an order of magnitude faster than for most specialized crawling cells. In addition, host cell invasion occurs within few seconds. These peculiar features prompted us to search for molecules underlying the formation of the motile force in tachyzoïtes of *Toxoplasma gondii*. The inventors have recently identified Toxofilin, a novel actin binding protein, as the major candidate for controlling actin dynamics in tachyzoïtes. Toxofilin has been purified in complex with parasite actin monomers and in vitro assays have demonstrated it regulates the competence of actin monomers to associate and of polymers to elongate. When Toxofilin was ectopically overexpressed as GFP-tagged protein in mammalian non-muscle cells it clearly disrupted the actin cytoskeleton and caused disassembly of actin stress fibers. In tachyzoites, Toxofilin binds G-actin and copurifies with a parasite F-actin containing fraction suggesting that it may control parasite actin dynamics as well. Such a role was further suggested by the highly variable localization pattern of Toxofilin in the moving parasite i.e. during gliding or host cell entry (see Poupel et al., 2000. Molecular Biology of the Cell, vol 11, pp 355–368).

SUMMARY OF THE INVENTION

The inventors recently became interested in looking at Toxofilin phosphorylation since Toxofilin sequence displays several <<consensus sites>> for phosphorylation. The inventors have shown that Toxofilin is in vitro and in vivo phosphorylated: the parasite kinase activity which phosphorylates Toxofilin is cytosolic, is recovered after heparin sepharose chromatography and is inhibited by either soluble heparin, DRB, or GTP, three common inhibitors of casein kinase II (CKII).

Investigating the phosphate turn over on Toxofilin, the inventors identified and biochemically characterized a type 2C phosphatase yet unidentified in *T. gondii* as a copurifying member of the G actin-Toxofilin complex. The inventors produced a recombinant PP2C which is a partial fragment of the PP2C protein and which contains 331 amino acids as well as a recombinant complete PP2C soluble and active on exogenous substrate (casein labeled with $^{32}P$ phosphate, see Materials and methods). Then, the inventors performed in vitro assays with this recombinant active PP2C and demonstrated that Toxofilin is a major substrate for type 2C phosphatase.

The invention covers the complete PP2C and its fragments as well as the corresponding nucleotidic sequences.

BRIEF DESCRIPTION OF THE DRAWINGS

FIG. 1 represents the nucleotide sequence (SEQ ID NO:1) and the 331 amino acid sequence (SEQ ID NO:2) of *Toxoplasma gondii* type 2C phosphatase.

FIG. 2 represents in square brackets the portion of the amino acid sequence of FIG. 1 (SEQ ID NO:2) fused to glutathione S transferase corresponding to the partial recombinant protein obtained by the Inventors.

FIGS. 3A–H are an alignment of the PPC2F amino acid sequences of *Toxoplasma gondii* and human genome (BLAST-plasmodatabase) (amino acids 61–325 of SEQ ID NO:2 with SEQ ID NO:3; amino acids 38–325 of SEQ ID NO:2 with SEQ ID NO:4; amino acids 143–328 of SEQ ID NO:2 with SEQ ID NO:5; amino acids 19–326 of SEQ ID NO:2 by itself; amino acids 141–294 of SEQ ID NO:2 with SEQ ID NO:6; amino acids 141–294 of SEQ ID NO:2 with SEQ ID NO:7; amino acids 109–327 of SEQ ID NO:2 with SEQ ID NO:8; amino acids 219–287 of SEQ ID NO:2 with SEQ ID NO:9; amino acids 116–331 of SEQ ID NO:2 with SEQ ID NO:10; amino acids 97–277 of SEQ ID NO:2 with SEQ ID NO:11; amino acids 182–327 of SEQ ID NO:2 with SEQ ID NO:12; and amino acids 121–183 of SEQ ID NO:2 with SEQ ID NO:13). This alignment shows that the catalytic site of each PP2C is conserved but that the remaining part of the sequences are different.

Figure 4:
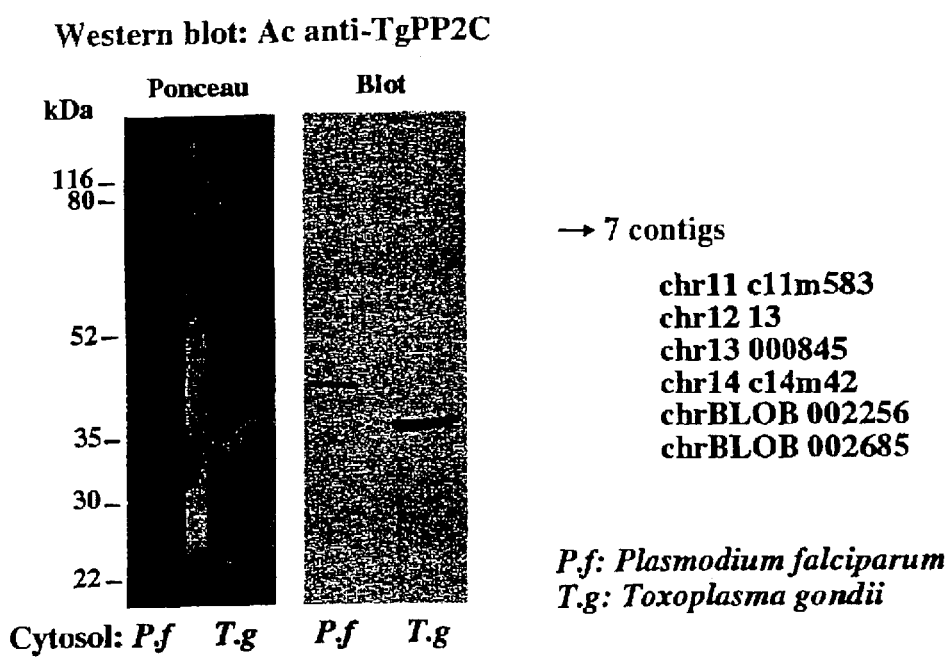
FIG. 4 represents a Western blot wherein PP2C proteins of *P. falciparum* and *T. gondii* are recognized by a polyclonal serum obtained after immunization of rabbit with a purified PP2C protein of *T. gondii*.
Figure 5A:
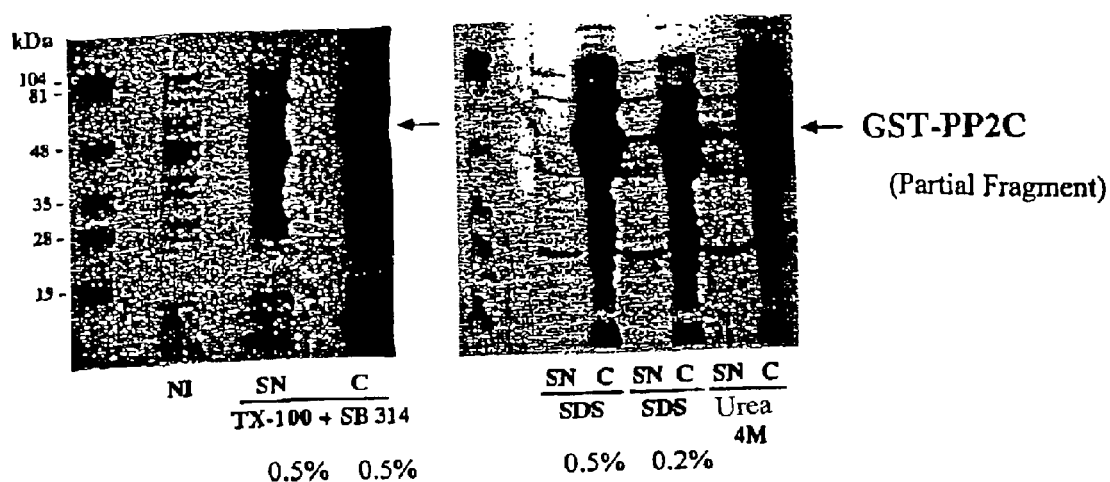
FIG. 5A—Solubilization test of GST-PP2C (partial fragment). A SDS gel of a fused protein GST-PP2C (partial fragment) shows a specific band.
Figure 5B:
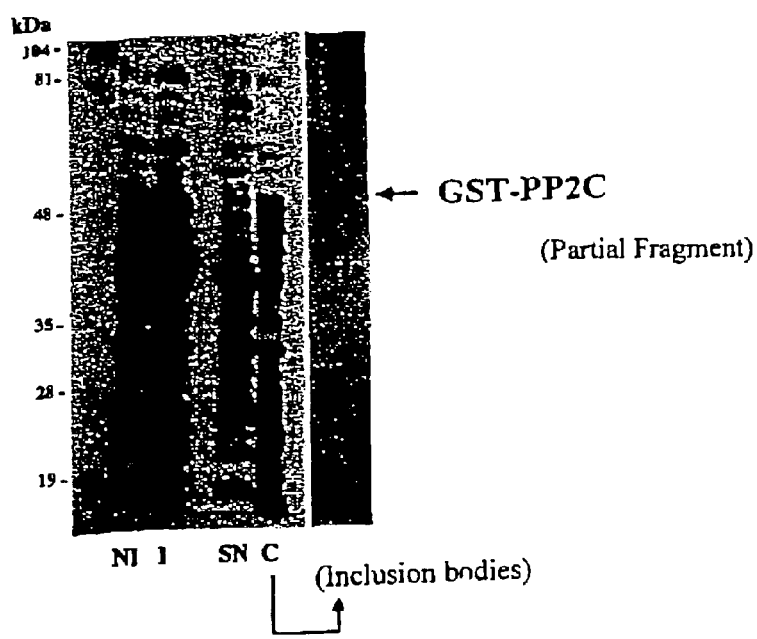
FIG. 5B—Purification of the inclusion bodies.
Figure 6:
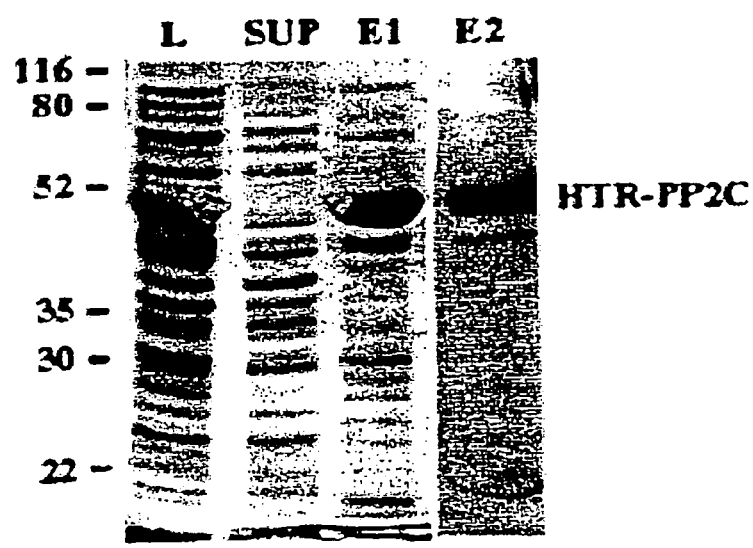
FIG. 6. Purification HTR-PP2C:SDS PAGE visualisation of eluates.

For the purification process, *E. coli* bacteria (strain BL21) have been incubated with 0.1 mM IPTG to induce the GST-PP2C containing plasmid to be expressed (1 hour, 25° C.). After expression, the bacteria were lysed in PBS containing 0.5% vol/vol Triton X100 and 0.5% vol/vol SB314. With this lysis protocol, all the GST-PP2C remained in the insoluble fraction within the inclusion bodies. The inclusion bodies were then purified by successive centrifugation and recovered some GST-PP2C as seen in the photo of the SDS-PAGE electrophoresis.

DESCRIPTION OF THE INVENTION

One object of the invention is an active molecule capable of modulating the activity of a native protein of a parasitic organism of the Apicomplexa phylum, wherein said molecule is endowed with serine-threonine phosphatase activity, or a fragment thereof A fragment of said molecule is peptidic sequence capable of being recognized by a polyclonal serum obtained after immunization of a rabbit with a purified PP2C protein of *T. gondii*.

In a preferred embodiment, the molecule endowed with serine-threonine phosphatase activity is a type 2C phosphatase (PP2C), and the parasitic organism of Apicomplexa phylum is selected from the group comprising *Toxoplasma gondii, Plasmodium falciparum* and *Crystosporidium parvum*.

Another object of the invention is a molecule for preventing or treating an infection due to a parasitic organism of the Apicomplexa phylum wherein said molecule modulates the interaction between a protein of said parasitic organism endowed with serine-threonine phosphatase activity and Toxofilin of said parasitic organism.

In a preferred embodiment, the protein of said parasitic organism endowed with serine-threonine phosphatase activity is a type 2C phosphatase (PP2C), and the parasitic organism of Apicomplexa phylum is selected from the group comprising *Toxoplasma gondii, Plasmodium falciparum* and *Crystosporidium parvum*.

The protein of said parasitic organism has a nucleic acid sequence and an amino acid sequence with sufficient identity compared to the sequence of FIG. 1 for being endowed with serine-threonine phosphatase activity. The active site corresponding to the enzymatic activity is located from amino acid 18 to amino acid 325 (included). The molecular weight is 37 kDa.

Another object of the invention is a method for screening molecules capable of modulating the activity of a native protein of a parasitic organism of the Apicomplexa phylum endowed with serine-threonine phosphatase activity wherein said method comprises the steps of:

a) possibly fixing a native or a recombinant Toxofilin of said parasitic organism to a matrix;

b) phosphorylating said Toxofilin with labeled ATP using a parasite kinase fraction or a recombinant casein kinase II;

c) controlling the phosphorylation of Toxofilin by labeling counting;

d) incubating the labeled Toxofilin with or without the molecule to be tested and adding a native or a recombinant serine-threonine phosphatase of said parasitic organism;

e) measuring the labeling;

wherein a variation of the labeling of the Toxofilin incubated with the molecule to be tested compared with the labeling of the Toxofilin incubated without the molecule to be tested is indicative of the capacity of the molecule to modulate said serine-threonine phosphatase activity of said protein.

In a preferred embodiment, the protein of said parasitic organism endowed with serine-threonine phosphatase activity is a type 2C phosphatase (PP2C), and the parasitic organism of Apicomplexa phylum is selected from the group comprising *Toxoplasma gondii, Plasmodium falciparum* and *Crystosporidium parvum*.

An other object of the invention in a molecule capable of modulating the activity of a native protein of a parasitic organism of the Apicomplexa phylum endowed with serine-threonine phosphatase activity which is capable to be screened by said method.

Another object of the invention is a method for screening molecules for preventing or treating an infection due to a parasitic organism of the Apicomplexa phylum wherein said method comprises the steps of:

f) possibly fixing a native or a recombinant Toxofilin of said parasitic organism to a matrix;

g) phosphorylating said Toxofilin with labeled ATP using a parasite kinase fraction or a recombinant casein kinase II;

h) controlling the phosphorylation of Toxofilin by labeling counting;

i) incubating the labeled Toxofilin with or without the molecule to be tested and adding a native or a recombinant serine-threonine phosphatase of said parasitic organism;

j) measuring the labeling;

wherein a decrease of the labeling of the Toxofilin incubated with the molecule to be tested compared with the labeling of the Toxofilin incubated without the molecule to be tested is indicative of the capacity of the molecule to prevent or treat an infection due to a parasitic organism of the Apicomplexa phylum.

In a preferred embodiment, the protein of said parasitic organism endowed with serine-threonine phosphatase activity is a type 2C phosphatase (PP2C), and the parasitic organism of Apicomplexa phylum is selected from the group comprising *Toxoplasma gondii, Plasmodium falciparum* and *Crystosporidium parvum*.

Another object of the invention is an active molecule for preventing or treating an infection due to a parasitic organism of the Apicomplexa phylum which is capable to be screened by said method.

Another object of the invention is an antibody directed against a native protein of a parasitic organism of the Apicomplexa phylum, said protein being endowed with serine-threonine phosphatase activity.

Another object of the invention is a method for preventing or treating an infection due to a parasite of the Apicomplexa phylum wherein said method comprise administration of a molecule of the invention.

EXAMPLES

In vivo $^{32}$P Orthophosphate Labeling of Tachyzoïte and Toxofilin Immunoprecipitation Purified transiently extracellular parasites were rinsed in phosphate and serum-free buffer (10 mM Tris-Cl pH 7.4, 150 mM NaCl, 5 mM KCl, 5 mM MgCl$_2$, 1.6 mM CaCl$_2$, 0.5% glucose, 0.1% bovine serum albumin) and incubated at $10^8$ per ml in the same medium supplemented with 500 µCi per ml of orthophosphoric acid (specific activity of 8.8 $10^9$ Ci per mmole from NEN life Science products, Inc) (120 min, 37° C., 5% CO$_2$). Unincorporated radioactive phosphate was then washed out by rinsing three times the parasites in 50 ml of phosphate and serum-free buffer. $10^9$ tachyzoïtes were lysed in 1 ml of [20 mM Tris-Cl pH 8.0, 50 mM KCl, 0.1 mM Ethyleneglycol-bis(β-aminoethyl)-N,N,N,N'-tetraacetic acid (EGTA), 0.1 mM Ethylenediamine-tetraacetic acid (EDTA)] supplemented with 0.5% (vol/vol) protease inhibitor stocks by 5 liquid nitrogen freezing and defreezing cycles. Lysates were centrifuged (10 min, 800×g, 4° C.) and the corresponding supernatants were first clarified (20 min, 20.000×g, 4° C.), then precleared on sepharose CL-4B (Pharmacia) (1 hour, 4° C.). After removal of the sepharose-bound protein fractions, the soluble fractions were successively incubated with Toxofilin antibodies (overnight, 4° C.) and with protein G-sepharose (1 hour, 23° C.). After successive washes in buffer A (50 mM Tris-HCl, pH 7.5, 150 mM NaCl) supplemented with 0.1% vol/vol TX-100 and 0.5% (wt/vol) serum albumin then supplemented only with 0.1% vol/vol TX-100 and a final wash in buffer A, the protein G-sepharose bound fraction was eluated in SDS-PAGE sample buffer. Eluates were boiled prior to a 12% acrylamide gel electrophoresis and radioactive scan of the dried gel.

Production of rToxofiline

The inventors used the expression vector pGEX6-P3 (Pharmacia) into which the full length Toxofilin encoding cDNA was cloned as described in Poupel et al. (2000) but to improve the yield of Toxofilin production, the protocol was slightly modified as follows. An *E. coli* clone (BL21 strain) positive for the plasmid was grown up to OD=1.2–1.4 and induced with isopropylthio-β-D-galactoside (0.1 mM, 1 hour, 25° C.). At the end of the induction period the bacteria were pelleted and subsequently lysed in buffer PBS$^-$ and sonicated (30 seconds, 4° C.). The lysate was supplemented with TX-100 (0.5% vol/vol) and N-tetradecyl-N,N-dimethyl-3 ammonio-1-propanesulfonate (0.5% wt/vol, Sigma) (15 min, 4° C.). The supernatant recovered after centrifugation (15.000×g, 15 min, 4° C.) was incubated with sepharose CL-4B (1 hour, 4° C.) and the unbound fraction was incubated with glutathione sepharose (Pharmacia) (4° C., overnight). The beads were washed with 30 bead volumes of PBS– containing 0.1% TX-100 and with 10 volumes of prescission cleavage buffer (50 mM Tris-HCl, pH 7.0, 150 mM NaCl, 1 mM EDTA, 1 mM dithiothreitol (DTT)). The bound GST-polypeptide was cleaved with pre-scission protease to recover the recombinant Toxofilin (r-Toxofilin) without GST (Pharmacia) (8 hours, 4° C.). Soluble r-Toxofilin was immunoprecipitated with anti-Toxofilin antibodies (overnight, 4° C.) and recovered on protein G-dynabeads (1 hour, 23° C.) (Dynal) before the kinase/phosphatase assay.

Identification and Cloning of *T. gondii* Type 2C Phosphatase (TgPP2C)

Native gel and Peptide microsequencing: The native gel was performed as described in Poupel et al (2000). The gel slice containing the 36 kDa actin-binding protein from the parasite was subjected to tryptic digestion (30° C., 18 hours, 0.3 mg of trypsin in 0.1 M Tris-HCl, pH 8.6; 0.01% (vol/vol) Tween 20). The tryptic peptides were recovered by HPLC on a DEAE and a C18 columns. The sequencing of two peptides gave respectively SVFDGTVGDFAQENV (SEQ ID NO:14) and NQSADNITAMTVFFK (SEQ ID NO:15) and the later was found in one clone from the *T. gondii* database of expressed sequence tags (EST, WashU-Merk Toxoplasma EST project).

cDNA library screening and DNA sequencing: Non-degenerate primers were synthesized for amplification of the target sequence from the clone identified as TgESTzy48A06.R1. The oligonucleotide with the sequence: 5'-AGTGCAGACAACATTACTGCGATG-3' (SEQ ID NO:16) corresponding to part of one peptide microsequence (SADNITAM-amino acids 3–10 of SEQ ID NO:15) was used as the up stream primer, while 5'-AGACACACCAAGAATCTCGTC-3' (SEQ ID NO:17) was chosen as the down stream primer in the TgEST clone. The PCR conditions for amplifiation of the 207 bp DNA product were as follows: a hot start of 2 mm at 94° C. by 35 cycles (45 sec, 94° C.; 30 sec, 53° C.; 30 sec, 72° C.) and a final elongation step at 72° C. for 10 min. The 207 bp fragment recovered was $^{32}$P-labeled using random priming (Megaprime kit, Amersham), purified on Sephacryl S-400 HR column (Pharmacia) and used as a probe to screen a *T. gondii* tachyzoite cDNA library (kindly provided by J. W. Ajioka, Cambridge, UK). After 2 round of screening, 12 independent overlapping clones were selected and their cDNA was prepared for nucleotide sequencing performed by Genset (France), using both vector and *T. gondii* sequence specific primers (Genset).

Biochemical Characterization of TgPP2C Activity

Phosphatase assays were carried out using 10 µM $^{32}$P-casein. Briefly, the reaction mixture in a total of 30 µl, consisted of 10 µl containing 100 ng protein of tachyzoïte cytosolic fraction (in 10 mM Tris-Cl pH 8.0, 150 mM NaCl, 0.1% vol/vol of protease inhibitors, 4° C.) plus 10 µl of phosphatase assay buffer (50 mM Tris-Cl pH 7.4, 0.5% β-mercaptoethanol, 0.1% BSA) containing the different effectors. 10 µl of labeled substrate ($^{32}$P-casein) was added to start the reactions (30 min, 30° C.) and 200 µl of 20% trichloracetic acid to stop them. The mixtures were centrifuged (5 min, 15.000×g) and 180 µl of the supernatant was directly counted for $^{32}$P radioactivity using a Cerenkov counter.

Production of a Thioredoxin-Hispatch Tg PP2C and Biochemical Characterization

The fragment for expression of TgPP2C was prepared by PCR amplification of a full length TgPP2C encoding cDNA, using primers introducing a EcoRI restriction site at position 5' and a XbaI restriction site at position 3'. For amplification of the upper strand: 5'-GCCGAATTCCCATGAAGTCCTCTGCTGAAATTAG-3' SEQ ID NO:18) and of the lower strand: 5'-GCCTCTAGACTAATCAGTCTTCTTGAAGAACACTG-3' (SEQ ID NO:19). The amplified fragment was cloned into the expression vector pThioHisB (Invitrogen) after digestion with EcoRI and XbaI of both fragment and vector. For expression of the ThioHis-TgPP2c, an *E. coli* clone (Top 10 strain) positive for the plasmid was grown up to OD=0.8 and induced with ispropylthio-β-D-galactoside (0.1 mM, 2 hours, 37° C.). At the end of the induction period, the bacteria were pelleted and subsequently lysed in buffer (20mM $NaH_2PO_4$, 500 mM NaCl, N-octylglucoside (0.5% vol/vol) supplemented with 0.1% (vol/vol) protease inhibitor stocks by sonnication (30 seconds, 4° C.). DNase was added to 2 µg/ml (30 min, 4° C.) following by centrifugation (10 min, 14.000×g 4° C.). The supernatant was chromatographied on a nickel column (Probond, Invitrogen) and the imidazole eluate was dialyzed before being chromatographied on a phenylarsineoxide-agarose column (Thiobond, Invitrogen). Mercaptoethanol eluates were dialyzed against 5 mM Tris-HCl, pH 7.5, 50 mM NaCl and stored aliquoted in 5% sucrose at −80° C. until use for testing the activity (see below).

Tachyzoïte Cytosol Preparation and Heparin Chromatography

Cytosol: Frozen tachyzoites ($10^9$) were thawed on ice and lysed by 5 liquid nitrogen freezing and defreezing cycles in 500 µl of kinase buffer (10 mM Tris-HCl, pH 7.5, 150 mM NaCl, 10 mM $MgCl_2$, 1 mM DTT) supplemented with 0.2% (vol/vol) protease inhibitor stocks. The extract was centrifuged (15 min, 800×g, 4° C.) to remove nuclei and unbroken cells. The supernatant was centrifuged (30 min, 100.000×g, 4° C.) in a TL100 table top ultracentrifuge (Beckman) using the TLA 100.3 rotor. The resulting cytosol was stored frozen at −80° C. in 100 µl aliquots until use.

Heparin chromatography: A cytosolic fraction from $10^9$ parasites was pre-cleared on sepharose CL-4B (1 hour, 4° C.), and subsequently chromatographied on heparin sepharose (Pharmacia) (1 hour, 4° C.). After several washes in 10 mM Tris-HCl, pH 7.5, 150 mM NaCl supplemented with 0.5% vol/vol TX-100, the heparin-bound proteins were recovered by a 0.5 M NaCl elution in 10 mM Tris-HCl, pH 7.5. The eluate was dialyzed against kinase buffer (overnight, 4° C.) prior to be used in kinase assay while the heparin unbound fraction (i.e.: flow through) was thoroughly recovered and stored at −80° C. Each lot was controlled for its activity on casein (see above).

Kinase and Phosphatase Assay on Toxofilin

Kinase reaction: 2 µg of immobilized rToxofilin on protein G-dynabeads were washed in kinase buffer before to be incubated with a tachyzoïte cytosolic fraction prepared in kinase buffer (µg of proteins in 100 µl) and precleared on protein G-dynabeads. The reaction was started by adding 100 µM of $Na_2$ ATP and 10 µCi of [$\gamma^{32}P$] ATP (3000 Ci/mmol, NEN life science product, Inc) (15 min, 30° C.). Unbound materials and unincorporated [$\gamma^{32}P$] ATP were washed out with 200 volumes of kinase buffer containing with TX-100 (0.5% vol/vol) followed by 100 volumes of kinase buffer. Toxofilin and bound proteins were eluted in SDS-PAGE sample buffer prior to electrophoresis and radio-activity scan (phosphoimager, Molecular Dynamics). Toxofilin phosphorylation was quantified using NIH Image Quant software.

To characterize the kinase activity responsible for Toxofilin phosphorylation, three types of experiments were carried out:

1) Pharmacological inhibitors such as heparin (20 µg per ml, Sigma), GTP (200 µM, Sigma), 5,6-dichloro-1-B-D-ribofuranosylbenzimidazole (100 µM, Calbiochem) or staurosporine (1 µM, Calbiochem) were added 15 min before starting the kinase reaction.

2) A fraction eluted after heparin chromatography of the cytosol and the corresponding unbound fraction (see above) were assayed for their respective kinase activity towards rToxofilin.

Phosphatase reaction: The purified recombinant TgPP2C dialyzed against kinase buffer was added (doses activité) either before to start the kinase assay or after the last wash in kinase buffer. In the latter case, control and test samples were incubated for 15 additional minutes (30° C.) before a final wash in kinase buffer. In some control experiments, one unit of a recombinant fragment of rabbit catalytic type 1 phosphatase (Up State Biotechnology) which is known to dephosphorylate several *T. gondii* tachyzoïte proteins was replacing TgPP2C. Eluates were treated as described for the kinase assay.

Tg PP2C Antibodies

A rabbit polyclonal antibody raised against the GST-partial PP2C was prepared and absorbed on GST to get only the PP2C reactive immunoglobulins. It has been initially raised using GST-partial PP2C separated in a polyacrylamide gel slice directly injected to rabbits (according to standard protocol of EUROGENTEC, 4 immunizations on day 0, 14, 28 and 56). Each immunization performed with a composition containing from 20 to 100 µg of PP2C which is a polypeptide comprising 265 amino acids from V64 to K328 included as referred in FIG. 2.

Protocol to Screen for PP2C Inhibitors

It is possible to covalently fix the recombinant Toxofilin to a matrix (resin or membrane), to phosphorylate it with $^{32}P$ Adenosine Tri Phosphateusing either an enriched parasite kinase fraction which is already available or even a recombinant casein kinase II from other source (see Materiel and Methods). Human casein kinase II works well at phosphorylating Toxofilin. In addition, the Inventors are presently cloning the *Toxoplasma* casein kinase II. Once phosphorylation has been controlled by radioactive counting, it is easy to incubate the sample ($^{32}P$-labelled Toxofilin) with or without (control) putative inhibitors and add recombinant PP2C. The criteria to analyze will be the radioactive counts and to observe if those counts have or have not decreased. An efficient phosphatase hydrolyses the $^{32}P$ phosphate which is then lost in the washes and consequently induces a decrease in radio-active counts. If the phosphatase activity is blocked by an inhibitor (either towards the catalytic site or affecting the 3D structure of the catalytic site), the $^{32}P$ phosphate will not be hydrolyzed. Such assay also allows quantitative analysis of the inhibitory effect towards the phosphatase activity.

Some flurogenic substrates have been recently developed as an alternative to radio-activity for several phosphatase activity dosages. One might think about incorporating such fluorochrome to Toxofilin. Additionally, other substrate such as casein are commonly used to assay phosphatase activity including PP2C activity.

Protocol to Screen for Inhibitors of the Host Cell Invasion by *Toxoplasma gondii*.

One feature of *Toxoplasma gondii* tachyzoïte is that it can enter virtually any kind of cells, making in vitro invasion assay quite simple to realize. It is also feasible to incubate tachyzoïtes with orthophosphate (see Materials and Methods) and at the same time expose or not them to different putative inhibitors (different doses . . . ).

In that case, it is possible to check if this/these inhibitor(s) affect the phosphorylation of Toxofilin (preparation of cytosol, immunoprecipitation of Toxofilin, electrophoresis and radioactive scanning to detect if Toxofilin has or not incorporated 32P).

For invasion assay, the tachyzoïtes can be resuspended in 2 ml of Dulbecco's MEM (usually $5×10^7$) supplemented with 2% of heat-inactivated foetal calf serum and expose to the putative inhibitors (different doses, duration . . . ) before being incubated with 70–80% confluent human foetal fibroblasts previously plated on glass coverslips (20 min, 37° C., 5% $CO_2$). It will be interesting to leave the inhibitor during the invasion assay (in case it is reversible) or to wash it off before the assay and finally to check any affect on the host cell.

After a short contact between parasites and host cell (15 to 30 min), both will be fixed in 2% paraformaldehyde in $PBS^-$ (15 min, 23° C.). Extracellular parasites will be stained with a monoclonal anti-P30 surface protein of *T. gondii* (40 μg/ml, Euromedex) and revealed using the Alexa488 anti-mouse IgG conjugate (Molecular probes) while both internalized and extracellular parasite will be vizualized by 4',6 Diamidino-2-phenylindole staining (DAPI, 5 μg/ml) under microscope. The number of cells containing parasites out of 100 cells randomly selected will be reported in triplicate for each treatment. In addition, for each coverslip, the number of internalized parasites per cell will be counted on 4 samples of 25 infected cells.

What is claimed is:

1. A method for screening molecules which inhibit the activity of native protein of a parasitic organism of the Apicomplexa phylum, having type 2C serine-threonine phosphatase activity, wherein said method comprises:

a) fixing a native or a recombinant Toxofilin of said parasitic organism to a matrix;

b) phosphorylating said Toxofilin with labeled ATP using a parasite kinase fraction or a recombinant casein kinase II;

c) controlling the phosphorylation of Toxofilin by labeling counting the phosphorylated and labeled Toxofilin;

d) incubating the labeled Toxofilin with or without the molecule to be tested and adding a type 2C serine-threonine phosphatase of said parasitic organism; and e) measuring the labeling;

wherein a variation of the labeling of the Toxofilin incubated with the molecule to be tested compared with the labeling of the Toxofilin incubated without the molecule to be tested is indicative of the capacity of the molecule to inhibit said type 2C serine-threonine phosphatase activity of said protein.

2. The method of claim 1, wherein the type 2C serine-threonine phosphatase of step d) is recombinant.

3. The method of claim 2, wherein the recombinant type 2C serine-threonine phosphatase is a fragment having type 2C serine-threonine phosphatase activity.

4. The method of claim 1, wherein the parasitic organism of Apicomplexa phylum is selected from the group comprising *Toxoplasma gondii, Plasmodium falciparum* and *Crystosporidium parvum.*

5. A method for screening molecules for treating an infection due to a parasitic organism of the Apicomplexa phylum wherein said method comprises:

a) fixing a native or a recombinant Toxofilin of said parasitic organism to a matrix;

b) phosphorylating said Toxofilin with labeled ATP using a parasite kinase fraction or a recombinant casein kinase II;

c) controlling the phosphorylation of Toxofilin by labeling counting the phosphorylated and labeled Toxofilin;

d) incubating the labeled Toxofilin with or without the molecule to be tested and adding a type 2C serine-threonine phosphatase of said parasitic organism; and e) counting the labeling;

wherein a decrease of the labeling of the Toxofilin incubated with the molecule to be tested compared with the labeling of the Toxofilin incubated without the molecule to be tested is indicative of the capacity of the molecule to treat an infection due to a parasitic organism of the Apicomplexa phylum.

6. The method of claim 5, wherein the type 2C serine-threonine phosphatase of step d) is recombinant.

7. The method of claim 6, wherein the recombinant type 2C serine-threonine phosphatase is a fragment having type 2C serine-threonine phosphatase activity.

8. The method of claim 5, wherein the parasitic organism of Apicomplexa phylum is selected from the group comprising *Toxoplasma gondii, Plasmodium falciparum* and *Crystosporidium parvum.*

* * * * *